(12) United States Patent
Botta et al.

(10) Patent No.: US 8,895,600 B2
(45) Date of Patent: Nov. 25, 2014

(54) NON PEPTIDIC 14-3-3 INHIBITORS AND THE USE THEREOF

(75) Inventors: Maurizio Botta, Siena (IT); Valentina Corradi, San Rocco-Roverè V.se (IT); Federico Falchi, Monterotondo Marittimo (IT); Manuela Mancini, Bologna (IT); Maria Alessandra Santucci, Bologna (IT)

(73) Assignee: Università degli Studi di Siena, Siena (IT)

( * ) Notice: Subject to any disclaimer, the term of this patent is extended or adjusted under 35 U.S.C. 154(b) by 0 days.

(21) Appl. No.: 13/571,065

(22) Filed: Aug. 9, 2012

(65) Prior Publication Data

US 2013/0203831 A1 Aug. 8, 2013

Related U.S. Application Data

(63) Continuation-in-part of application No. PCT/IB2011/050640, filed on Feb. 16, 2011.

(60) Provisional application No. 61/304,977, filed on Feb. 16, 2010.

(51) Int. Cl.
| | | |
|---|---|---|
| *A01N 43/56* | (2006.01) | |
| *A61K 31/415* | (2006.01) | |
| *C07D 401/00* | (2006.01) | |
| *C12Q 1/48* | (2006.01) | |
| *G01N 33/573* | (2006.01) | |
| *A61K 31/4152* | (2006.01) | |
| *G01N 33/574* | (2006.01) | |
| *A61K 31/4035* | (2006.01) | |
| *A61K 31/196* | (2006.01) | |

(52) U.S. Cl.
CPC ............ *A61K 31/4152* (2013.01); *C12Q 1/485* (2013.01); *G01N 33/573* (2013.01); *G01N 33/57426* (2013.01); *A61K 31/4035* (2013.01); *A61K 31/196* (2013.01)
USPC ........................................ 514/404; 546/276.1

(58) Field of Classification Search
USPC ........................................ 514/404; 546/276.1
See application file for complete search history.

(56) References Cited

U.S. PATENT DOCUMENTS

2003/0149015 A1 8/2003 Barrett et al.

FOREIGN PATENT DOCUMENTS

| EP | 2116523 A1 | 11/2009 |
|---|---|---|
| WO | 198/45242 A1 | 10/1998 |
| WO | 00/76489 A2 | 12/2000 |

OTHER PUBLICATIONS

Hermeking, H. "The 14-3-3 Cancer Connection" Nature Reviews, Dec. 2003, vol. 3, pp. 931-943.*
Foote et al. "Review Article 14-3-3 proteins in neurological disorders" Int. J Biochem Mol Biol, Jun. 2012, vol. 3, No. 2, pp. 152-164.*
Sheridan, R.P. "The Most Common Chemical Replacements in Drug-Like Compounds" J. Chem. Inf. Comput. Sci, 2002, vol. 42, pp. 103-108.*
J. G. Cannon Chapter Nineteen in Burger's Medicinal Chemistry and Drug Discovery, Fifth Edition, vol. I: Principles and Practice, Wiley-Interscience 1995, pp. 783-802, 784.*
Liao, Wenqiang, et al.: "14-3-3 Proteins regulate glycogen synthase 3 beta phosphorylation and inhibit cardiomyocyte hypertrophy", FEBS Journal, Blackwell Publishing, London, GB, vol. 272, No. 8, Apr. 1, 2005, pp. 1845-1854.
Wang, B., et al: "Isolation of high-affinity peptide antagonists of 14-3-3 proteins by phage display", Biochemistry, American Chemical Society, US, vol. 38, No. 38, Sep. 21, 1999, pp. 12499-12504.
Mhawech, Paulette: "14-3-3 proteins—an update", Cell Research, vol. 15, No. 4, Apr. 2005, pp. 228-236.

* cited by examiner

*Primary Examiner* — Kendra D Carter
(74) *Attorney, Agent, or Firm* — Lucas & Mercanti, LLP

(57) ABSTRACT

The present invention refers to compounds with inhibitory activity against 14-3-3 proteins and their use in the treatment of tumors, in particular chronic myeloid leukemia. The invention also provides methods for the identification of 14-3-3 protein inhibitors.

3 Claims, 7 Drawing Sheets

Asinex commercial database (gold, platinum, sinergy and emerald) 2D structure.

↓
- Format conversion, hydrogen elimination and hydrogen treatment (All-atom with No-L)
- Ligprep with neutralize, tautomerize and pre-filter: 100<MW<800, HBA<=10, HBD<=5 chiral center<=2
- Qikprop
- Epik (pH 7.0 +- 2.0 no tautomeri)
- Ligprep to optimize the molecules treated by Epik
- Duplicates elimination Compounds 3D

Fig. 3

NON PEPTIDIC 14-3-3 INHIBITORS AND THE USE THEREOF

CROSS-REFERENCE TO RELATED APPLICATIONS

This application is a continuation-in-part of PCT International Application Serial No. PCT/IB2011/050640, filed Feb. 16, 2011, which claims the benefit of priority from U.S. Provisional Application Ser. No. 61/304,977, filed Feb. 16, 2010, the contents of which are incorporated herein by reference.

FIELD OF THE INVENTION

The present invention refers to compounds with inhibitory activity against 14-3-3 proteins and their use in the treatment of chronic myeloid leukemia. The invention also provides two methods for the identification of 14-3-3 protein inhibitors. These methods consist of virtual screening techniques performed using (a) a structure-based pharmacophore model approach or (b) a virtual docking approach.

The invention relates to the identification by molecular modeling approaches of small molecules and the use thereof, in particular as inhibitors of 14-3-3 proteins.

BACKGROUND OF THE INVENTION

Tyrosine kinase inhibitors, such as Imatinib, are currently used as effective and frontline therapy for chronic-phase of chronic myeloid leukemia (CML). However, despite the generally positive response to the clinical therapy, the resistance to Imatinib represents a serious problem in the treatment of patients expressing the Bcr-Abl fusion gene, resulting from the juxtaposition of the c-Abl proto-oncogene on chromosome 9 to Bcr sequences on chromosome 22. The identification of Imatinib-resistant Bcr-Abl mutations has led to a rapid development of new generations of Bcr-Abl inhibitors with distinct mechanisms of action (Leukemia, 2008, 22, 572-577). The clinical activity of these new derivatives, such as AMN107 and SKI606, is currently evaluated in ongoing Phase I/II clinical trials, while Dasatinib, a dual Src/Abl inhibitor, has received FDA approval for clinical treatment of Imatinib-resistant CML patients (Cancer Cell. 2005, 7, 129-141; Curr Pharm Biotechnol. 2006, 7, 371-379; Clin Ther. 2007, 29, 2289-2308). However, although these agents are in general very active in treating Imatinib-resistant CML, they fail to overcome the Imatinib resistance caused by the T315I mutation. This mutation, occurring at the gatekeeper position of the Abl kinase domain, is responsible for about 15% of Imatinib-resistant CML patients and it is considered the biggest obstacle for CML treatment, especially in advanced phases of the disease. In the last few years, multiple efforts have been focused on the development of new Bcr-Abl inhibitors targeting this mutant. Recently, two Aurora kinase inhibitors, VX-680 (Cancer Res. 2006, 66, 1007-1014) and PHA-739358 (Nat. Rev. Cancer 2007, 7, 345-356) and the new compound PPY-A (Chem. Biol. Drug Des. 2007, 70, 171-181) have been reported as effective against the deleterious mutations at the gatekeeper position. Since their discovery, many other novel agents have been developed, i.e., SGX393 (Proc. Natl. Acad. Sci. USA. 2008, 105, 5507-5512).

To attenuate Bcr-Abl transforming potential and overcome drug resistance, much interest is addressed toward development of new and complementary therapeutic strategies targeting pathways directly involved in the regulation of causative events of CML. In this context, the authors of the present invention focused their efforts on studying 14-3-3 proteins and their relationship with CML. 14-3-3s were the first proteins described as phosphoserine or phosphothreonine binding modules (Seminars in Cancer Biology 2006, 16, 173-182). In human, seven distinct isoforms have been identified ($\beta$, $\gamma$, $\epsilon$, $\eta$, $\sigma$, $\tau$, and $\zeta$, corresponding to the entries P31946, P68981, P62258, Q04917, P31947, P27348, and P29310 of the UniProtKB/Swiss-Prot database, respectively) and they constitute a family of highly conserved and ubiquitously expressed proteins, acting as homo or heterodimers. The initial observation that the binding to 14-3-3 family members requires ligand phosphorylation emerged from work on tryptophan hydroxylase (Biochem. Biophys. Res. Commun. 1993, 194, 144-149) and Raf, the upstream activator of the classical MAP kinase pathway (Mol. Cell. Biol. 1995, 15, 3390-3397). Subsequent studies of the 14-3-3 binding sites on Raf (Cell. 1996, 84, 889-897), together with oriented peptide library screening on all mammalian 14-3-3s (Cell. 1997, 91, 961-971), led to the identification of two main 14-3-3 consensus motifs. These motifs correspond to the sequences RSX-pS/T-XP (mode I) and RXXX-pS/T-XP (mode II), where pS/T denotes a phosphorylated Serine or Threonine residue and X any amino acid, and they recognized by all 14-3-3 isotypes. 14-3-3s bind a large number of protein targets involved in the regulation of many intracellular processes, such as cell cycle progression, protein trafficking, signal transduction, cytoskeletal rearrangements, metabolism, transcriptional regulation of gene expression. 14-3-3s play also an important role in the coordination and the regulation of DNA damage response and apoptosis (Cell Cycle 2005, 4, 777-779; Seminars in Cancer Biology 2006, 16 162-172; Leukemia 2008, 22, 572-577). In this regard, c-Abl plays an important intermediary role in inducing apoptosis cell death (Nature Cell Biology 2005, 7, 213-214; Nature Cell Biol. 2005, 7, 278-285; Cell Cycle 2005, 4, 777-779; EMBO J. 2006, 25, 3774-3783). In fact, normally, c-Abl can shuttle between the cytoplasm and nucleus by classical mechanisms referring to the presence of three nuclear localization signals (NLSs) and one nuclear export signal (NES) in c-Abl carboxy-terminal region (entry P00519 of the UniProtKB/Swiss-Prot database). Into the nucleus, c-Abl can induce apoptosis in response to DNA damage, demonstrating that its intracellular localization is a crucial aspect in causing either the survival or apoptosis of the cell. In normal cells, the cytoplasmatic localization of c-Abl is due to the binding with 14-3-3 proteins. In fact, in the sequence of c-Abl is present a consensus motif for this protein family, located between the second (residues 707-720 of Abl sequence) and the third (residues 759-772 of Abl sequence) NLS, corresponding to the sequence RSV-T(735)-LP (entry P00519 of the UniProtKB/Swiss-Prot database). Mutagenesis studies on Thr735 of Abl revealed that this sequence, after phosphorylation on this threonine residue, allows the binding to 14-3-3s in such a way that c-Abl is sequestered into the cytoplasm (Nature Cell Biol. 2005, 7, 278-285). Upon DNA damage, a mechanism involving c-Jun N-terminal kinase (Jnk) is activated in order to phosphorylate 14-3-3s on specific serine residues, inducing both c-Abl release from 14-3-3s and its localization into the nucleus to activate apoptosis cell death (Nature Cell Biol. 2005, 7, 278-285; Nature Cell Biol. 2005, 7, 213-214).

The oncogenic form of Abl kinase, Bcr-Abl, is constitutively activated and localizes primarily to the cytoplasm (J. Clin. Invest. 1993, 92, 1925-1939) where it elicits anti-apoptotic signals and confers survival. With regard to the mechanism of association and dissociation between c-Abl and 14-3-3, the fusion protein Bcr-Abl interferes in many ways. First of all, Bcr-Abl prevents the translocation of c-Abl into the nucleus in response to ionizing radiations by inhibiting the phosphorylation by Jnk of 14-3-3$\sigma$ at Ser186. In CML cells, in fact, it was demonstrated that Jnk kinase binds to the Bcr-Abl/HDAC1 complex more efficiently than to the complex c-Abl/14-3-3$\sigma$, precluding or reducing its ability to phosphorylate 14-3-3$\sigma$ and to release c-Abl. In addition, Bcr- Abl affects the complete activation of Jnk preventing its phosphorylation at Thr183, indispensable for the subsequent phosphorylation of 14-3-3. Experimental evidences indicate that inhibition of the fusion protein enzymatic activity by the inhibitor Imatinib is followed by phosphorylation of 14-3-3σ at Ser186 and of Jnk at Thr183, resulting in the translocation of c-Abl into the nuclear compartment. Secondly, Bcr-Abl in CML cells induces a massive over-expression of 14-3-3σ through an epigenetic regulation (hyper-acetylation of histone H4) of 14-3-3 promoter. R18 is a peptide inhibitor of 14-3-3 (Biochemistry, 1999, 38, 12499-12504). Once this peptide is bound to the 14-3-3 binding site, proteins with a consensus motif for 14-3-3 can not interact with 14-3-3s. In this context, R18, bound to 14-3-3 binding site, prevents the binding of c-Abl that can be, in that way, translocated into the nucleus to induce apoptosis. Moreover, with regard to the previously described effect of Bcr-Abl on the over-expression of 14-3-3σ, the inhibition of Bcr-Abl mediated by Imatinib resulted in persistent deacetylation of histone H4 at 14-3-3σ promoter, with a significant reduction in the amount of 14-3-3σ protein expression. This aspect can facilitate the translocation into the nucleus of the c-Abl protein (Traffic, 2009, 10, 637-647).

All together these results suggest that i) targeting the 14-3-3σ binding site with molecules able to affect the interactions with the protein target, and with Abl in particular, and ii) simultaneously inhibiting Bcr-Abl oncoprotein, can represent an alternative and/or complementary therapeutic strategy to treat CML.

At the present time, only R18 is used as an inhibitor of 14-3-3 proteins to block the binding between 14-3-3s and their target. In the present invention, computational methodologies were applied to identify non peptidic compounds able to disrupt the interaction between 14-3-3s and their protein ligands, and in particular, between 14-3-3σ and c-Abl. The biological effects of the identified compounds were tested in cellular assays in order to verify their mechanism of action. In particular, clonogenic assays, evaluations of apoptotic cell death and measurements of nuclear translocation of c-Abl were performed.

SUMMARY OF THE INVENTION

A new challenge in CML is the development of alternative and complementary therapeutic strategies to overcome the resistance that can occur against the traditional drugs. 14-3-3 protein family plays a role in a wide variety of cell signaling processes including the apoptosis regulation through a way involving Abl tyrosine kinase. In fact, c-Abl kinase, retained in the cytoplasm by binding to 14-3-3 proteins, can shuttle into the nucleus to induce apoptosis after DNA damage, while the oncogenic Bcr-Abl, in consequence of its cytoplasmatic location, promotes proliferation and survival of CML progenitors. Moreover, Bcr-Abl induces an overexpression of 14-3-3σ isoform and prevents, in that way, DNA-damage-induced nuclear import of residual normal c-Abl protein.

In the present invention, a computational methodology based on the development of a structure-based pharmacophoric model built using the crystallographic structure of the human 14-3-3σ isoform in complex with a mode I-binding motif phosphopeptide was applied.

This invention describes new 14-3-3 inhibitors having affinity for 14-3-3 active site and preventing the binding with c-Abl. They represent the first non-peptidic inhibitors targeting 14-3-3 proteins and as such are a helpful strategy to enhance the effects of traditional inhibitors of the oncogenic Bcr-Abl protein.

It is therefore an object of the invention to provide a compound of formula I for medical use:

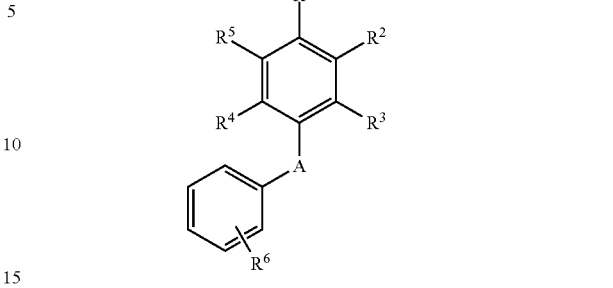

Formula I wherein
A is nitrogen NH and it is single bonded to all atoms to which it is attached.
$R^1$, $R^2$, $R^3$, $R^4$ and $R^5$ are each independently hydrogen, —COOH, —NO$_2$, OH, methyl, ethyl or halogen,
$R^6$ is hydrogen, methyl, C1-C8 alkyl optionally substituted with one or more $R^{11}$, or —C(=O)O—(C1-C6 alkyl), —C(=O)O—(C1-C7 alkyl), —C(=O)O—(C1-C8 alkyl) wherein the C1-C6 alkyl and C1-C7 alkyl and C1-C8 alkyl groups may optionally contain one or two $R^{11}$ substituents. $R^6$ can also be —C(=O)O—(C1-C2 alkyl)-phenyl-CH$_3$ or —SO$_2$NH-phenyl-$R^{12}$, wherein $R^{11}$ is methyl and $R^{12}$ is methyl or ethyl or —COOH or —NO$_2$, or —COO-ethyl or halogen.

In a preferred embodiment, the compound of formula I is the compound BV-01:

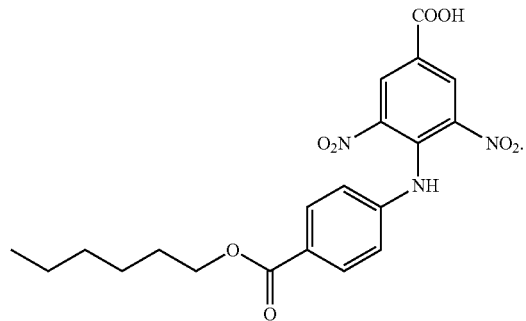

BV-01

It is another object of the invention to provide a compound of formula II for medical use:

Formula II wherein
A is NH and it is single bonded to all atoms to which it is attached or C=O,
B is C=O, CH$_2$ or NH;

when B is C=O or CH$_2$, A is NH;
when B is NH, A is C=O;
C is carbon or nitrogen;
D, E, F, G are each independently carbon, nitrogen, sulphur or oxygen;
the bond between C and G can be single or double;
when C, D, E, F, G are each independently nitrogen, they are single bonded to all atoms to which they are attached;
when D, E, F, G are each independently sulphur or oxygen R$^6$, R$^7$, R$^8$, R$^9$ are absent;
R$^1$, R$^2$, R$^3$, R$^4$ and R$^5$ are each independently hydrogen, —COOH, —NO$_2$, OH, methyl, ethyl or halogen;
R$^6$, R$^7$, R$^8$, R$^9$ may be present or not, if present, they are methyl, ethyl, phenyl or naphthyl;
when D, E, F, G are each independently carbon, R$^6$, R$^7$, R$^8$, R$^9$ may also be OH or oxygen, in the case of oxygen, the bond between oxygen and the carbon is double;
when R$^6$, R$^7$, R$^8$, R$^9$ are each independently phenyl or naphthyl, they can optionally be substituted with R$^{10}$ wherein R$^{10}$ is methyl, hydroxyl or halogen.

Preferably, the compound of formula II is the compound BV-02:

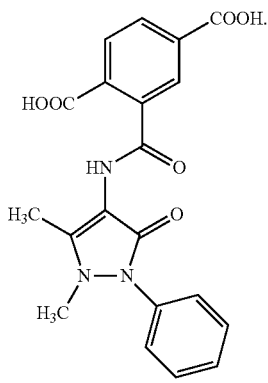

BV-02

It is an object of the invention to provide a compound of formula III for medical use:

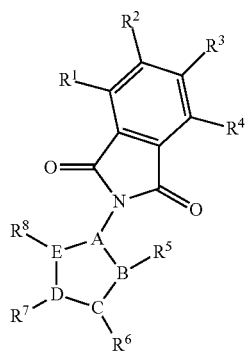

Formula III wherein
A is carbon or nitrogen;
B, C, D, E are each independently carbon, nitrogen sulphur or oxygen;
the bond between A and E can be single or double;
when A, B, C, D, E are each independently nitrogen, they are single bonded to all atoms to which they are attached;
when B, C, D, E are each independently sulphur or oxygen R$^5$, R$^6$, R$^7$, R$^8$ are absent;

R$^1$, R$^2$, R$^3$, R$^4$ are each independently hydrogen, —COOH, —NO$_2$, OH, methyl, ethyl or halogen;
R$^5$, R$^6$, R$^7$, R$^8$ may be present or not, if present, they are methyl, ethyl, phenyl, or naphthyl,
when B, C, D, E are each independently carbon, R$^5$, R$^6$, R$^7$, R$^8$, may also be OH or oxygen, in the case of oxygen, the bond between oxygen and the carbon is double;
when R$^5$, R$^6$, R$^7$, R$^8$ are each independently phenyl or naphthyl, they can optionally be substituted with R$^9$ wherein R$^9$ is methyl, hydroxyl, or halogen.

It is another object of the present invention to provide a compound of formula IV for medical use:

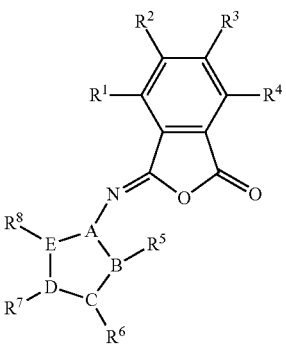

Formula IV wherein
A is carbon or nitrogen;
B, C, D, E are each independently carbon, nitrogen sulphur or oxygen;
the bond between A and E can be single or double;
when A, B, C, D, E are each independently nitrogen, they are single bonded to all atoms to which they are attached;
when B, C, D, E are each independently sulphur or oxygen R$^5$, R$^6$, R$^7$, R$^8$ are absent;
R$^1$, R$^2$, R$^3$, R$^4$ are each independently hydrogen, —COOH, —NO$_2$, OH, methyl, ethyl or halogen;
R$^5$, R$^6$, R$^7$, R$^8$ may be present or not, if present, they are methyl, ethyl, phenyl, or naphthyl,
when B, C, D, E are each independently carbon, R$^5$, R$^6$, R$^7$, R$^8$, may also be OH or oxygen, in the case of oxygen, the bond between oxygen and the carbon is double;
when R$^5$, R$^6$, R$^7$, R$^8$ are each independently phenyl or naphthyl, they can optionally be substituted with R$^9$ wherein R$^9$ is methyl, hydroxyl, or halogen.

It is a further object of the invention to provide a compound of formula V for medical use:

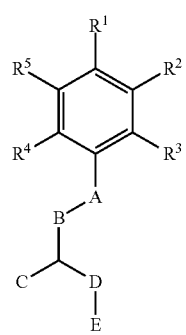

Formula V wherein
R¹, R², R³, R⁴ and R⁵ are each independently hydrogen, —COOH, —NO₂, OH, or methyl, ethyl or halogen;
A is NH and it is single bonded to all atoms to which it is attached or C=O;
B is C=O, CH₂ or NH;
when B is C=O or CH₂, A is NH;
when B is NH, A is C=O;
C is hydrogen or methyl;
D is S or CH₂;
E may be E₁, E₂, E₃ or E₄.
If E is E₁ of the formula:

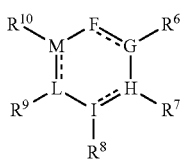

Formula E₁

E is bonded to D through F;
dashed bonds may be single or double bonds;
F, G, H, I, L and M are each independently carbon or nitrogen;
If G is nitrogen and is double bonded to F, R⁶ is absent;
If H is nitrogen and is double bonded to I, R⁷ is absent;
If I is nitrogen and is double bonded to H, R⁸ is absent;
If L is nitrogen and is double bonded to M, R⁹ is absent;
If M is nitrogen and is double bonded to L, R¹⁰ is absent;
R⁶, R⁷, R⁸, R⁹ and R¹⁰ are each independently methyl, ethyl, propyl, iso-propyl, halogen, CN, methoxyl, hydrogen, cyclopropyl, phenyl, —COOH, —NO₂, —COO-ethyl, naphthyl;
when R⁶, R⁷, R⁸, R⁹ and R¹⁰ are each independently phenyl or naphthyl, they can optionally be substituted with R¹¹, wherein R¹¹ is methyl, ethyl, —COOH, —NO₂, —COO-ethyl or halogen.
If E is E₂ of the formula:

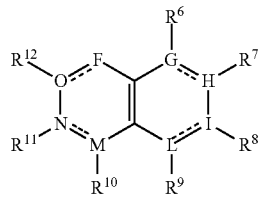

Formula E₂

E is bonded to D through F;
dashed bonds may be single or double bonds;
F, G, H, I, L, M, N, and O are each independently carbon or nitrogen;
If G is nitrogen and is double bonded to H, R⁶ is absent;
If H is nitrogen and is double bonded to G, R⁷ is absent;
If I is nitrogen and is double bonded to L, R⁸ is absent;
If L is nitrogen and is double bonded to I, R⁹ is absent;
If M is nitrogen and is double bonded to N, R¹⁰ is absent;
If N is nitrogen and is double bonded to M, R¹¹ is absent;
If O is nitrogen and is double bonded to F, R¹² is absent;
R⁶, R⁷, R⁸, R⁹, R¹⁰, R¹¹, and R¹² are each independently methyl, ethyl, propyl, iso-propyl, halogen, CN, methoxyl, hydrogen, cyclopropyl, phenyl, —COOH, —NO₂, —COO-ethyl, naphthyl;
when R⁶, R⁷, R⁸, R⁹, R¹⁰, R¹¹, and R¹² are each independently phenyl or naphthyl, they can optionally be substituted with R¹³, wherein R¹³ is methyl, ethyl, —COOH, —NO₂, —COO-ethyl or halogen.

If E is E₃ of the formula:

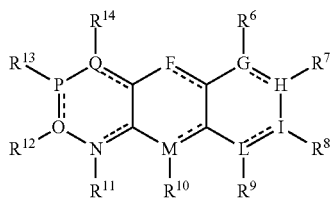

Formula E₃

E is bonded to D through F;
dashed bonds may be single or double bonds;
F, G, H, I, L, M, N, O, P and Q are each independently carbon or nitrogen;
If G is nitrogen and is double bonded to H, R⁶ is absent;
If H is nitrogen and is double bonded to G, R⁷ is absent;
If I is nitrogen and is double bonded to L, R⁸ is absent;
If L is nitrogen and is double bonded to I, R⁹ is absent;
If M is nitrogen and is double bonded to the carbon, R¹⁰ is absent;
If N is nitrogen and is double bonded to the carbon, R¹¹ is absent;
If O is nitrogen and is double bonded to P, R¹² is absent;
If P is nitrogen and is double bonded to O, R¹³ is absent;
If Q is nitrogen and is double bonded to the carbon, R¹⁴ is absent;
R⁶, R⁷, R⁸, R⁹, R¹⁰, R¹¹, R¹², R¹³ and R¹⁴ are each independently methyl, ethyl, propyl, iso-propyl, halogen, CN, methoxyl, hydrogen, cyclopropyl, phenyl, —COOH, —NO₂, —COO-ethyl, naphthyl;
when R⁶, R⁷, R⁸, R⁹, R¹⁰, R¹¹, R¹², R¹³ and R¹⁴ are each independently phenyl or naphthyl, they can optionally be substituted with R¹⁵, wherein R¹⁵ is methyl, ethyl, —COOH, —NO₂, —COO-ethyl or halogen.
If E is E₄ of the formula reported below:

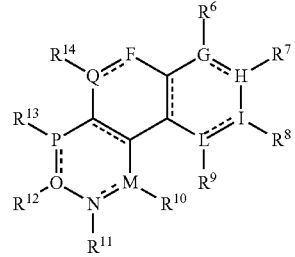

Formula E₄

E is bonded to D through F;
dashed bonds may be single or double bonds;
F, G, H, I, L, M, N, O, P and Q are each independently carbon or nitrogen;
If G is nitrogen and is double bonded to H, R⁶ is absent;
If H is nitrogen and is double bonded to G, R⁷ is absent;
If I is nitrogen and is double bonded to L, R⁸ is absent;
If L is nitrogen and is double bonded to I, R⁹ is absent;
If M is nitrogen and is double bonded to N, R¹⁰ is absent;
If N is nitrogen and is double bonded to M, R¹¹ is absent;
If O is nitrogen and is double bonded to P, R¹² is absent;
If P is nitrogen and is double bonded to O, R¹³ is absent;
If Q is nitrogen and is double bonded to F, R¹⁴ is absent;
R⁶, R⁷, R⁸, R⁹, R¹⁰, R¹¹, R¹², R¹³ and R¹⁴ are each independently methyl, ethyl, propyl, iso-propyl, halogen, CN, methoxyl, hydrogen, cyclopropyl, phenyl, —COOH, —NO₂, —COO-ethyl, naphthyl;

when $R^6$, $R^7$, $R^8$, $R^9$, $R^{10}$, $R^{11}$, $R^{12}$, $R^{13}$ and $R^{14}$ are each independently phenyl or naphthyl, they can optionally be substituted with $R^{15}$, wherein $R^{15}$ is methyl, ethyl, —COOH, —NO₂, —COO-ethyl or halogen.

In a preferred embodiment, the compounds of the invention are endowed with a 14-3-3 family protein inhibitor activity.

Preferably, the compound of the invention is for use as an anti-tumor agent, still preferably the tumor is chronic myeloid leukemia (CML) or Imatinib-resistant chronic myeloid leukemia.

It is a further object of the invention to provide a pharmaceutical composition comprising the compound of the invention or a pharmaceutically acceptable salt, solvate, or hydrate thereof and pharmaceutically acceptable carrier, diluents or excipients.

It is an object of the invention to provide a method to identify a compound endowed with 14-3-3 inhibitory activity comprising:

(a) providing a computer readable medium including a representation of the pharmacophore model shown in FIG. 1 and having the coordinates shown in Tables 1 and 2;

(b) providing a candidate compound;

(c) comparing the three-dimensional structure of the candidate compound with the three-dimensional structure of said pharmacophore; and (d) selecting a compound that conforms to the features of the pharmacophore;

(e) computationally evaluating the level of binding of the selected compound with the binding site of the crystal structure of the human 14-3-3 (PDB 1YWT), wherein if a sufficient level of binding is found, then the compound endowed with 14-3-3 inhibitory activity is identified.

Preferably, the candidate compound as defined above is selected from a library of compounds, selected from a from a database, is provided computationally, is designed de novo or is designed from a known 14-3-3 inhibitor.

Preferably, the sufficient level of binding is indicated by a calculated binding energy defined by a ChemScore value of at least 35.

It is another object of the invention to provide a method to identify a compound endowed with 14-3-3 inhibitory activity comprising:

(a) providing a candidate compound; and (b) computationally evaluating the level of binding of the candidate compound with the binding site of BV-01 docked into the crystal structure of the human 14-3-3 (PDB 1YWT), wherein if a sufficient level of binding is found, then the compound endowed with 14-3-3 inhibitory activity is identified.

Preferably, the candidate compound as defined above is provided from a compound library comprising compounds having a sum of a penalty score between 0 and 1, wherein the penalty score is calculated based on at least HBD, HBA, rotatable bonds, SSSR (smallest set of smallest rings), maximum ring size, number of halogens, molecular weight, log P as indicated in Table 3.

Still more preferably, the sufficient level of binding is indicated by a calculated binding energy defined by a ChemScore value of at least 35 and a minimum distance 4 Å and an average distance ≤10 Å wherein the distance is the distance in respect to residue R129 of 14-3-3σ.

It is an object of the invention to provide a compound identified with the methods of the invention.

Preferably, the compound has the formula I, II, III, IV or V.

Still more preferably, the compound is for medical use.

It is another object of the invention to provide a composition comprising the compound as defined above, or a pharmaceutically acceptable salt, solvate, or hydrate thereof and pharmaceutically acceptable carrier, diluents or excipients.

It is a further object of the invention to provide a method for treating a tumor pathology, preferably a chronic myeloid leukemia, more preferably an Imatinib-resistant chronic myeloid leukemia. The method includes administering a therapeutic effective amount of the compound of the invention or of the composition of the invention to a patient or subject, e.g., human or other mammal, in need of such treatment.

Depending on the type and severity of the disease, about 2 mg/kg to 200 mg/kg of the compound of the invention is a candidate dosage for administration to the patient, whether, for example, by one or more separate administrations, or by continuous infusion. Preferably 20 mg/kg to 60 mg/kg is the candidate dosage. For repeated administrations over several days or longer, depending on the condition, the treatment is sustained until a desired suppression of disease symptoms occurs. However, other dosage regimens may be useful. The progress of this therapy is easily monitored by conventional techniques and assays.

The compound composition should be formulated, dosed, and administered in a fashion consistent with good medical practice. The compounds/derivatives of the present invention can be administered by any appropriate route. This includes (but is not limited to) intraperitoneal, intramuscular, intravenous, subcutaneous, intraarticular, intratracheal, oral, enteral, parenteral, intranasal or dermal administration. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the compound to be administered will be governed by such considerations, and is the minimum amount necessary to prevent, ameliorate, or treat a disease or disorder. The compound need not be, but is optionally formulated with one or more agents currently used to prevent or treat the disorder in question. The effective amount of such other agents depends on the amount of compound present in the formulation, the type of disorder or treatment, and other factors discussed above.

BRIEF DESCRIPTION OF THE DRAWINGS

The invention will be now described by means of non limiting examples referring to the following figures:

FIG. 3. Schematic representation of the protocol applied to build the 3D molecular database then used in the virtual screening approach.

DETAILED DESCRIPTION OF THE INVENTION

EXAMPLE 1

The computational methodology applied in the present invention was based on the development of a structure-based pharmacophoric model built using the crystallographic structure of the human 14-3-3σ isoform in complex with a mode I-binding motif phosphopeptide (1YWT entry of the Protein data bank, J. Biol. Chem. 2005, 280, 18891-18898). Structure-based virtual screening usually involves docking of compounds into a protein binding site using docking algorithms, followed by application of ranking of selected compounds to identify potential hits. However, several recent studies have shown that pharmacophore-based search in combination with docking-based virtual screening can improve the probability of identifying putative candidates (J. Med. Chem. 2005, 48, 3749-3755). In fact, the use of pharmacophore-based searches before docking studies can significantly narrow down the number of compounds to be analyzed, allowing a more exhaustive docking together with a more accurate investigation of their binding modes. In the present invention, the structure-based pharmacophore model was used as a search query to screen a database of commercially available compounds. After the application of such filter, in order to reduce the number of selected compounds and to retrieve the most "drug-like" ones, i.e the most potentially therapeutic compounds, Lipinski's Rule of Five (Adv. Drug Delivery Rev. 1997, 23, 3-25; Methods 2000, 44, 235-249) were applied. Finally, docking studies were performed using the set of compounds derived from the virtual screening protocol. Fourteen compounds were bought and tested to confirm their mechanism of action.

Description of the Structure-Based Pharmacophoric Model

The mode I-phosphopeptide in complex with 14-3-3σ isoform in PDB entry 1YWT is nine amino acids long and the phosphoresidue corresponds to a serine residue (MARSH-pS-YPA). Taking into account the channel shape of the binding site and the peptide length, a large number of interactions were identified in the complex by generating a first pharmacophore model by means of LigandScout 1.0 software (Pure Appl. Chem. 2004, 76, 991-996; Inteligand GmbH, Vienna, Austria, http://www.inteligand.com/ligandscout). The number of features of this pharmacophoric model was then reduced on the basis of literature data. Moreover, a Molecular Dynamics (MD) simulation was applied as a tool to reduce the pharmacophore model complexity, with the aim to investigate the stability of the interactions corresponding to Hydrogen Bond Donor (HBD) and Hydrogen Bond Acceptor (HBA) pharmacophoric features. Since hydrogen bonds were involved in this kind of interactions, the distance between the two heavy atoms and the angle defined by the acceptor, hydrogen and donor atoms were monitored during the MD. Only interactions for which the distance and the angle values stabilized to default values to form hydrogen bonds were retrieved.

Figure 1:
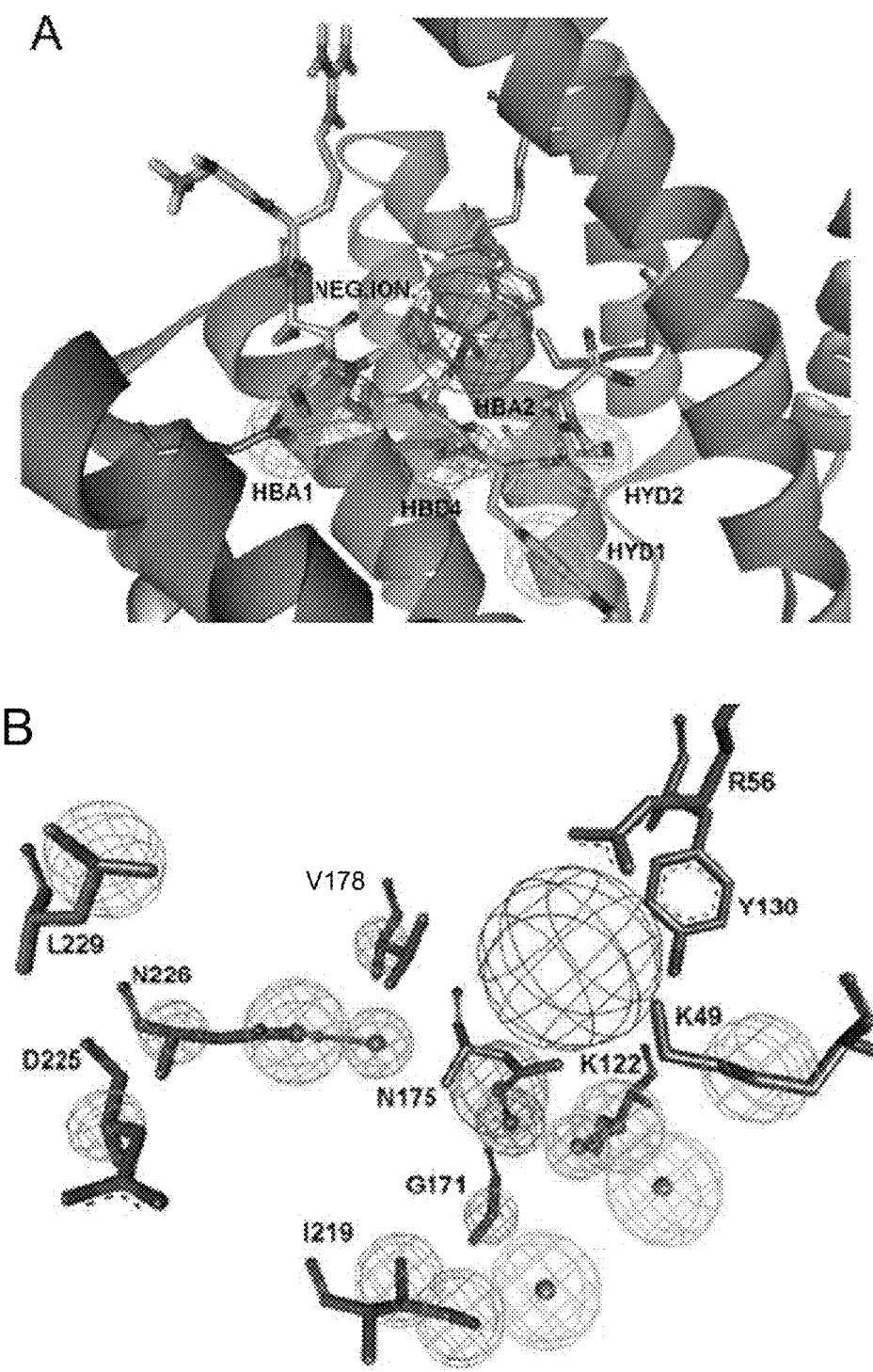
FIG. 1. Final pharmacophore model after Molecular Dynamics (MD) simulation. A. The pharmacophore model and the peptide used to generate it. B. The pharmacophore model together with the excluded-volumes.

At the end of MD analysis, the final pharmacophore model constituted of (FIG. 1, Table 1 and 2):
  Two HBA features, named HBA1 and HBA2. HBA1 refers to the interaction between CO of His5 backbone of the peptide and Asn226 side chain of σ isoform. HBA2 refers to the interaction between CO of Tyr7 backbone of the peptide and Lys122 side chain of a isoform.
  One HBD feature, named HBD4. HBD4 refers to the interaction between NH of Tyr7 backbone of the peptide and Asn175 side chain of a isoform.
  One negative ionisable feature, centered on the phosphate group of the peptide, with a tolerance value sets to 2.8 Å.
  Two hydrophobic features, named HYD1 and HYD2, corresponding to the aromatic ring of Tyr7 and to the aliphatic group of Pro8 of the peptide, respectively.
  Eight excluded volumes added for side chains of Leu229, Val178, Asn226, Asp225, Gly171, Ile219, Lys49.

TABLE 1

Coordinates of the pharmacophoric model features.

|  | Position | | | |
| --- | --- | --- | --- | --- |
|  | x | y | z | Radius |
| EV1 | 5.572 | 3.422 | 67.493 | 1.5 |
| EV2 | 9.523 | 0.022 | 71.457 | 1.0 |
| EV3 | 7.629 | −1.357 | 68.465 | 1.0 |
| EV4 | 7.855 | −3.625 | 60.641 | 1.0 |
| EV5 | 19.454 | 2.466 | 56.642 | 1.5 |
| EV6 | 17.51 | −5.79 | 67.036 | 1.5 |
| EV7 | 19.715 | −5.419 | 66.267 | 1.5 |
| EV8 | 17.772 | −7.091 | 62.872 | 1.0 |
| HYD1 | 20.727 | −2.497 | 63.972 | 1.6 |
| HYD2 | 20.573 | −0.607 | 59.894 | 1.7 |
| NEG. ION. | 13.762 | 1.298 | 58.347 | 2.8 |

|  | Tail | | | | Head | | | |
| --- | --- | --- | --- | --- | --- | --- | --- | --- |
|  | x | y | z | Radius | x | y | z | Radius |
| HBA1 | 11.731 | −0.955 | 63.849 | 1.1 | 10.078 | −2.192 | 66.025 | 1.6 |
| HBA2 | 17.991 | −3.026 | 60.217 | 1.2 | 18.235 | −5.176 | 58.139 | 1.7 |
| HBD4 | 16.128 | −1.648 | 61.911 | 1.1 | 14.561 | −3.93 | 60.755 | 1.7 |

EV, excluded volume;
HYD, hydrophobic feature;
NEG. ION. negative ionizable feature;
HBA and HBD, hydrogen bond acceptor and donor features.
Radius is indicated in Å.

TABLE 2

Distance matrix of the pharmacophore model. For HBA and HBD, distances have been computed referring to the tail.

|  | EV1 | EV2 | EV3 | EV4 | EV5 | EV6 | EV7 | EV8 | HYD1 | HYD2 | NEG. ION. | HBA1 | HBA2 | HBD4 |
| --- | --- | --- | --- | --- | --- | --- | --- | --- | --- | --- | --- | --- | --- | --- |
| EV1 |  |  |  |  |  |  |  |  |  |  |  |  |  |  |
| EV2 | 7.196 |  |  |  |  |  |  |  |  |  |  |  |  |  |
| EV3 | 5.756 | 3.8 |  |  |  |  |  |  |  |  |  |  |  |  |
| EV4 | 10.363 | 1.536 | 8.149 |  |  |  |  |  |  |  |  |  |  |  |
| EV5 | 18.443 | 18.062 | 17.153 | 13.698 |  |  |  |  |  |  |  |  |  |  |
| EV6 | 15.889 | 10.823 | 10.924 | 11.781 | 13.416 |  |  |  |  |  |  |  |  |  |
| EV7 | 17.578 | 12.666 | 12.938 | 13.249 | 12.445 | 2.365 |  |  |  |  |  |  |  |  |
| EV8 | 17.496 | 13.869 | 12.924 | 10.74 | 11.532 | 4.37 | 4.254 |  |  |  |  |  |  |  |
| HYD1 | 17.562 | 13.708 | 13.894 | 13.344 | 8.943 | 5.53 | 3.851 | 5.572 |  |  |  |  |  |  |
| HYD2 | 18.166 | 16.006 | 15.543 | 13.093 | 4.612 | 9.341 | 8.032 | 7.665 | 4.497 |  |  |  |  |  |
| NEG. ION. | 13.138 | 13.837 | 12.126 | 8.024 | 6.056 | 11.823 | 11.970 | 10.341 | 9.724 | 7.24 |  |  |  |  |
| HBA1 | 9.148 | 7.982 | 6.188 | 5.696 | 11.104 | 8.181 | 9.461 | 8.666 | 9.128 | 9.692 | 6.283 |  |  |  |
| HBA2 | 16.571 | 14.399 | 13.349 | 10.163 | 6.714 | 7.374 | 6.731 | 4.86 | 4.676 | 3.553 | 6.331 | 7.528 |  |  |
| HBD4 | 13.799 | 11.728 | 10.737 | 8.6 | 7.467 | 6.733 | 6.787 | 5.766 | 5.111 | 4.991 | 5.194 | 4.855 | 2.87 |  |

Virtual Screening and Selected Compounds

The model as described above was used as a search query to screen the Asinex Gold Collection, a database of over 200000 commercially available compounds (Asinex Gold Collection, Asinex Ltd., Moscow, Russia; http://www.asinex.com/libraries_gold.html), by means of the Fast Flexible search routine of Catalyst. A second filter based on Lipinkski's Rule of Five was then applied. GOLD software was used as a tool to dock the compounds selected by the previous steps, using ChemScore scoring function (J. Mol. Biol. 1995, 245, 43-53; J. Mol. Biol. 1997, 267, 727-748; Proteins 2003, 52, 609-623). A cluster analysis was performed for each compound, and the conformations belonging to more populated clusters associated with better score values were kept as possible binding modes for the selected compounds. Moreover, selected poses for each molecules were then re-ranked using X-Score program, based on a scoring function mainly applied to structure-based drug design studies (J. Computer.-Aided Mol. Des. 2002, 16, 11-26). Compounds were collected if the best conformation from ChemScore corresponded to the best one in X-Score.

In this study, docking results were also analyzed on the basis of a Molecular Interaction Field (MIF) computation (Software GRID, Grid 22, Molecular Discovery Ltd. Pinner, Middlesex, UK; http://www.moldiscovery.com), carried out for five different probes chosen to well characterize the main interactions between the proteins and a putative ligand. In particular, hydrophobic probes (DRY termed the hydrophobic probe and C1, corresponding to a methyl group), a hydrogen bond acceptor (O, a sp2 carbonyl oxygen) and a hydrogen bond donor (N1, a neutral flat NH group), and the phosphate probe (PO4) were chosen. Then, the points of minimum of MIFs (minima) were calculated, thus identifying the regions of most favourable interaction between each probe and the protein.

Finally, the results of docking studies for the selected compounds were compared with the distribution of these minima into the binding site. Compounds whose docking pose fitted at least three features of the pharmacophore model and which are in agreement with the localization of the minima were retrieved for subsequent biological assays.

Figure 2:
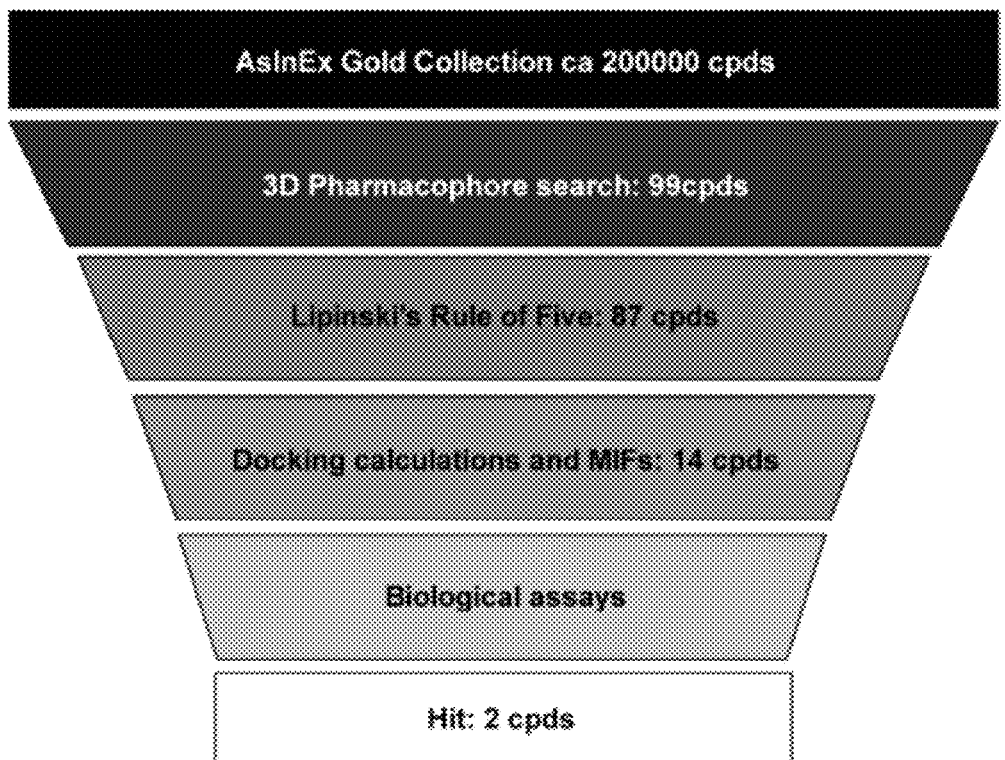
FIG. 2. Flowchart followed during high throughput virtual screening procedure.

A flowchart depicting the various steps of the virtual screening, including the database filtration and subsequent docking studies, is shown in FIG. 2.

After the biological evaluations, two hit compounds have been identified among the selected compounds. These hit compounds are named BV-01 and BV-02. Their formulas are reported below:

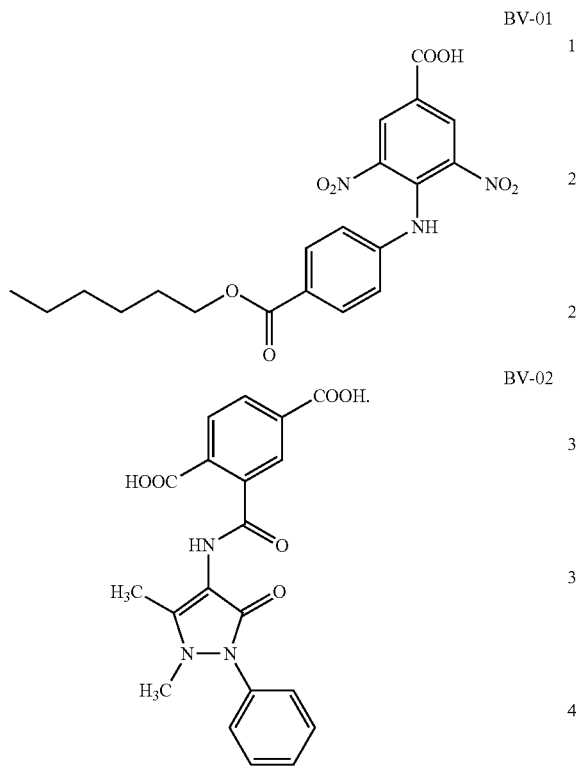

The virtual screening approach described in this study provided compounds with general formula I, II, III, IV or V:

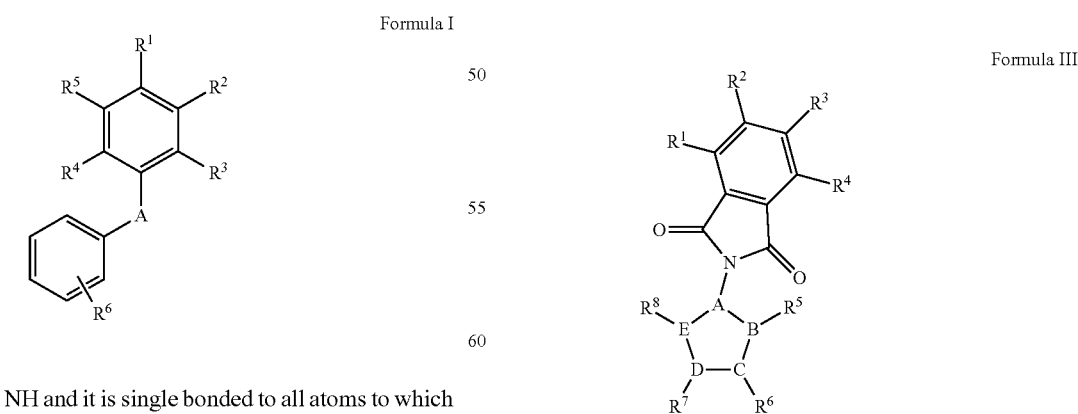

—C(=O)O—(C1-C7 alkyl), —C(=O)O—(C1-C8 alkyl) wherein the C1-C6 alkyl and C1-C7 alkyl and C1-C8 alkyl groups may optionally contain one or two $R^{11}$ substituents. $R^6$ can also be —C(=O)O—(C1-C2 alkyl)-phenyl-CH$_3$ or —SO$_2$NH-phenyl-$R^{12}$, wherein $R^{11}$ is methyl and $R^{12}$ is methyl or ethyl or —COOH or —NO$_2$, or —COO-ethyl or halogen;

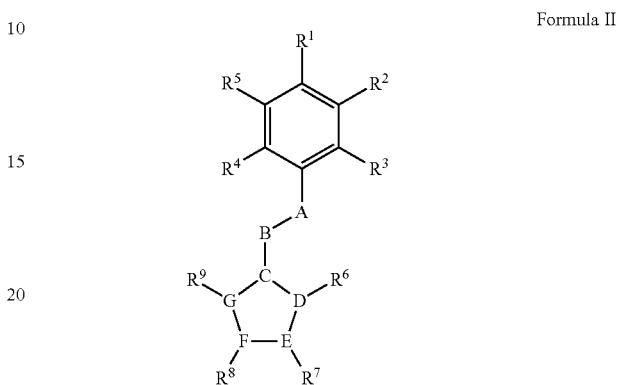

wherein
A is NH and it is single bonded to all atoms to which it is attached or C=O,
B is C=O, CH$_2$ or NH;
when B is C=O or CH$_2$, A is NH;
when B is NH, A is C=O;
C is carbon or nitrogen;
D, E, F, G are each independently carbon, nitrogen, sulphur or oxygen;
the bond between C and G can be single or double;
when C, D, E, F, G are each independently nitrogen, they are single bonded to all atoms to which they are attached;
when D, E, F, G are each independently sulphur or oxygen $R^6$, $R^7$, $R^8$, $R^9$ are absent;
$R^1$, $R^2$, $R^3$, $R^4$ and $R^5$ are each independently hydrogen, —COOH, —NO$_2$, OH, methyl, ethyl or halogen;
$R^6$, $R^7$, $R^8$, $R^9$ may be present or not, if present, they are methyl, ethyl, phenyl or naphthyl;
when D, E, F, G are each independently carbon, $R^6$, $R^7$, $R^8$, $R^9$ may also be OH or oxygen, in the case of oxygen, the bond between oxygen and the carbon is double;
When $R^6$, $R^7$, $R^8$, $R^9$ are each independently phenyl or naphthyl, they can optionally be substituted with $R^{10}$ wherein $R^{10}$ is methyl, hydroxyl or halogen;

wherein
A is nitrogen NH and it is single bonded to all atoms to which it is attached;
$R^1$, $R^2$, $R^3$, $R^4$ and $R^5$ are each independently hydrogen, —COOH, —NO$_2$, OH, methyl, ethyl or halogen,
$R^6$ is hydrogen, methyl, C1-C8 alkyl optionally substituted with one or more $R^{11}$, or —C(=O)O—(C1-C6 alkyl), wherein
A is carbon or nitrogen;
B, C, D, E are each independently carbon, nitrogen sulphur or oxygen;

the bond between A and E can be single or double;
when A, B, C, D, E are each independently nitrogen, they are single bonded to all atoms to which they are attached;
when B, C, D, E are each independently sulphur or oxygen $R^5, R^6, R^7, R^8$ are absent;
$R^1, R^2, R^3, R^4$ are each independently hydrogen, —COOH, —NO$_2$, OH, methyl, ethyl or halogen;
$R^5, R^6, R^7, R^8$ may be present or not, if present, they are methyl, ethyl, phenyl, or naphthyl,
when B, C, D, E are each independently carbon, $R^5, R^6, R^7, R^8$, may also be OH or oxygen, in the case of oxygen, the bond between oxygen and the carbon is double;
when $R^5, R^6, R^7, R^8$ are each independently phenyl or naphthyl, they can optionally be substituted with $R^9$ wherein $R^9$ is methyl, hydroxyl, or halogen;

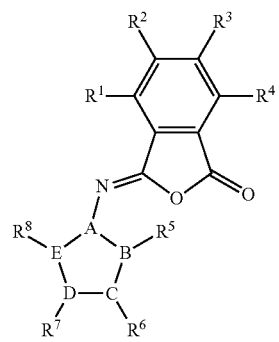

Formula IV wherein
A is carbon or nitrogen;
B, C, D, E are each independently carbon, nitrogen sulphur or oxygen;
the bond between A and E can be single or double;
when A, B, C, D, E are each independently nitrogen, they are single bonded to all atoms to which they are attached;
when B, C, D, E are each independently sulphur or oxygen $R^5, R^6, R^7, R^8$ are absent;
$R^1, R^2, R^3, R^4$ are each independently hydrogen, —COOH, —NO$_2$, OH, methyl, ethyl or halogen;
$R^5, R^6, R^7, R^8$ may be present or not, if present, they are methyl, ethyl, phenyl, or naphthyl,
when B, C, D, E are each independently carbon, $R^5, R^6, R^7, R^8$, may also be OH or oxygen, in the case of oxygen, the bond between oxygen and the carbon is double;
when $R^5, R^6, R^7, R^8$ are each independently phenyl or naphthyl, they can optionally be substituted with $R^9$ wherein $R^9$ is methyl, hydroxyl, or halogen;

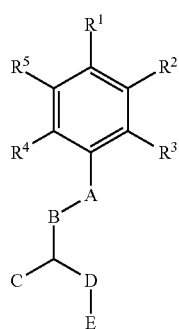

Formula V wherein
$R^1, R^2, R^3, R^4$ and $R^5$ are each independently hydrogen, —COOH, —NO$_2$, OH, or methyl, ethyl or halogen;

A is NH and it is single bonded to all atoms to which it is attached or C=O,
B is C=O, CH$_2$ or NH;
when B is C=O or CH$_2$, A is NH;
when B is NH, A is C=O;
C is hydrogen or methyl;
D is S or CH$_2$;
E may be $E_1, E_2, E_3$ or $E_4$:
If E is $E_1$ of the formula:

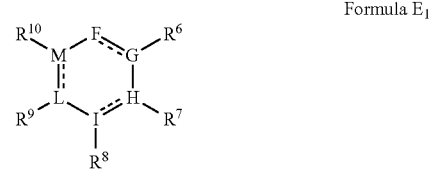

Formula $E_1$

E is bonded to D through F;
dashed bonds may be single or double bonds;
F, G, H, I, L and M are each independently carbon or nitrogen;
If G is nitrogen and is double bonded to F, $R^6$ is absent;
If H is nitrogen and is double bonded to I, $R^7$ is absent;
If I is nitrogen and is double bonded to H, $R^8$ is absent;
If L is nitrogen and is double bonded to M, $R^9$ is absent;
If M is nitrogen and is double bonded to L, $R^{10}$ is absent;
$R^6, R^7, R^8, R^9$ and $R^{10}$ are each independently methyl, ethyl, propyl, iso-propyl, halogen, CN, methoxyl, hydrogen, cyclopropyl, phenyl, —COOH, —NO$_2$, —COO-ethyl, naphthyl;
when $R^6, R^7, R^8, R^9$ and $R^{10}$ are each independently phenyl or naphthyl, they can optionally be substituted with $R^{11}$, wherein $R^{11}$ is methyl, ethyl, —COOH, —NO$_2$, —COO-ethyl or halogen;
If E is $E_2$ of the formula:

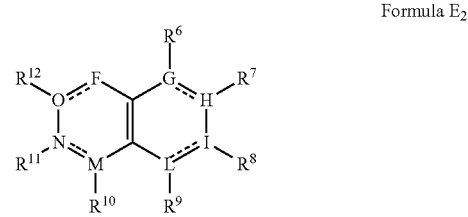

Formula $E_2$

E is bonded to D through F;
dashed bonds may be single or double bonds;
F, G, H, I, L, M, N, and O are each independently carbon or nitrogen;
If G is nitrogen and is double bonded to H, $R^6$ is absent;
If H is nitrogen and is double bonded to G, $R^7$ is absent;
If I is nitrogen and is double bonded to L, $R^8$ is absent;
If L is nitrogen and is double bonded to I, $R^9$ is absent;
If M is nitrogen and is double bonded to N, $R^{10}$ is absent;
If N is nitrogen and is double bonded to M, $R^{11}$ is absent;
If O is nitrogen and is double bonded to F, $R^{12}$ is absent;
$R^6, R^7, R^8, R^9, R^{10}, R^{11}$, and $R^{12}$ are each independently methyl, ethyl, propyl, iso-propyl, halogen, CN, methoxyl, hydrogen, cyclopropyl, phenyl, —COOH, —NO$_2$, —COO-ethyl, naphthyl;
when $R^6, R^7, R^8, R^9, R^{10}, R^{11}$, and $R^{12}$ are each independently phenyl or naphthyl, they can optionally be substituted with $R^{13}$, wherein $R^{13}$ is methyl, ethyl, —COOH, —NO$_2$, —COO-ethyl or halogen.

If E is $E_3$ of the formula:

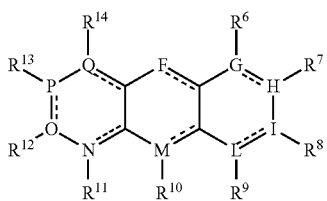

Formula $E_3$

E is bonded to D through F;
dashed bonds may be single or double bonds;
F, G, H, I, L, M, N, O, P and Q are each independently carbon or nitrogen;
If G is nitrogen and is double bonded to H, $R^6$ is absent;
If H is nitrogen and is double bonded to G, $R^7$ is absent;
If I is nitrogen and is double bonded to L, $R^8$ is absent;
If L is nitrogen and is double bonded to I, $R^9$ is absent;
If M is nitrogen and is double bonded to the carbon, $R^{10}$ is absent;
If N is nitrogen and is double bonded to the carbon, $R^{11}$ is absent;
If O is nitrogen and is double bonded to P, $R^{12}$ is absent;
If P is nitrogen and is double bonded to O, $R^{13}$ is absent;
If Q is nitrogen and is double bonded to the carbon, $R^{14}$ is absent;
$R^6$, $R^7$, $R^8$, $R^9$, $R^{10}$, $R^{11}$, $R^{12}$, $R^{13}$ and $R^{14}$ are each independently methyl, ethyl, propyl, iso-propyl, halogen, CN, methoxyl, hydrogen, cyclopropyl, phenyl, —COOH, —NO$_2$, —COO-ethyl, naphthyl;
when $R^6$, $R^7$, $R^8$, $R^9$, $R^{10}$, $R^{11}$, $R^{12}$, $R^{13}$ and $R^{14}$ are each independently phenyl or naphthyl, they can optionally be substituted with $R^{15}$, wherein $R^{15}$ is methyl, ethyl, —COOH, —NO$_2$, —COO-ethyl or halogen.
If E is $E_4$ of the formula reported below:

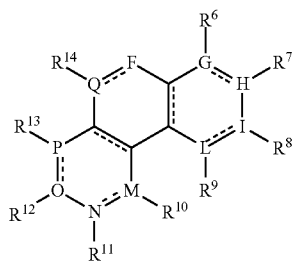

Formula $E_4$

E is bonded to D through F;
dashed bonds may be single or double bonds;
F, G, H, I, L, M, N, O, P and Q are each independently carbon or nitrogen;
If G is nitrogen and is double bonded to H, $R^6$ is absent;
If H is nitrogen and is double bonded to G, $R^7$ is absent;
If I is nitrogen and is double bonded to L, $R^8$ is absent;
If L is nitrogen and is double bonded to I, $R^9$ is absent;
If M is nitrogen and is double bonded to N, $R^{10}$ is absent;
If N is nitrogen and is double bonded to M, $R^{11}$ is absent;
If O is nitrogen and is double bonded to P, $R^{12}$ is absent;
If P is nitrogen and is double bonded to O, $R^{13}$ is absent;
If Q is nitrogen and is double bonded to F, $R^{14}$ is absent;
$R^6$, $R^7$, $R^8$, $R^9$, $R^{10}$, $R^{11}$, $R^{12}$, $R^{13}$ and $R^{14}$ are each independently methyl, ethyl, propyl, iso-propyl, halogen, CN, methoxyl, hydrogen, cyclopropyl, phenyl, —COOH, —NO$_2$, —COO-ethyl, naphthyl;
when $R^6$, $R^7$, $R^8$, $R^9$, $R^{10}$, $R^{11}$, $R^{12}$, $R^{13}$ and $R^{14}$ are each independently phenyl or naphthyl, they can optionally be substituted with $R^{15}$, wherein $R^{15}$ is methyl, ethyl, —COOH, —NO$_2$, —COO-ethyl or halogen.

EXAMPLE 2

Database Preparation

A 3D molecular database has been built starting from 2D commercial databases (Asinex Gold, Platinum, Synergy and Emerald Collections, Asinex Ltd., Moscow, Russia; http://www.asinex.com/libraries.html), by means of Schrödinger molecular modeling suite (https://www.schrodinger.com), as described in FIG. 3.

In order to retrieve in the 3D database only the most "drug-like" compounds, the following parameters have been taken into account:
Alkyl chains $\leq$ —(CH$_2$)$_6$CH$_3$;
No perfluorinated chains: —CF$_2$CF$_2$CF$_3$
At least one N or O atom;
HBD $\leq$5
HBA $\leq$10
Rotatable bonds $\leq$15
SSSR (smallest set of smallest rings) $\leq$6,
maximum ring size $\leq$7 members,
number of halogens $\leq$7,
100$\leq$ molecular weight $\leq$800 g mol$^{-1}$,
Log P $\leq$7.

For each of these parameters, a penalty has been calculated from an empiric function as described in Mol Divers. 2006, 10, 389-403 ("drug like" penalties) and reported in Table 3.

TABLE 3

| Functions used in drug-like and lead-like scores, according to Mol. Divers. 2006, 10, 389-403 | | |
|---|---|---|
| | 'Drug-like' penalties | 'Lead-like' penalties |
| HBD | $\leq$3.5: 0<br>>3.5 and <6.5: 0.3333 *P − 1.1667<br>$\geq$6.5: 1 | — |
| HBA | $\leq$7: 0<br>>7 and <13: 0.1667 *P − 1.667<br>$\geq$13: 1 | $\leq$63: 0<br>>6.3 and <11.7: 0.1852 *P − 1.1667<br>$\geq$11.7: 1 |
| Rotatable bonds | $\leq$10.5: 0<br>>10.5 and <19.5: 0.1111 *P − 1.1667<br>$\geq$18.5: 1 | $\leq$7: 0<br>>7 and <13: 0.1667 *P − 1.1667<br>$\geq$13: 1 |

TABLE 3-continued

Functions used in drug-like and lead-like scores, according to Mol. Divers. 2006, 10, 389-403

|  | 'Drug-like' penalties | 'Lead-like' penalties |
|---|---|---|
| Number of SSSR | ≤4.2: 0<br>>4.2 and <7.8: 0.2778 *P − 1.1667<br>≥7.8: 1 | ≤2.8: 0<br>>2.8 and <5.2: 0.4167 *P − 1.1667<br>≥5.2: 1 |
| Maximum ring size | ≤6: 0<br>>6 and <9.1: 0.3226 *P − 1.9355<br>≥9.1: 1 | — |
| Number of halogens | ≤4.9: 0<br>>4.9 and <9.1: 0.2381 *P − 1.1667<br>≥9.1: 1 | — |
| MW | ≤100: 1<br>>100 and <150: −0.02 *P + 3<br>≥150 and ≤350: 0<br>>350 and <800: 0.0022 *P − 0.7778<br>≥800: 1 | ≤100: 1<br>>100 and <150: −0.02 *P + 3<br>≥150 and ≤322: 0<br>>322 and <588: 0.0038 *P − 1.2105<br>≥588: 1 |
| Log P | ≤−5: 1<br>>−5 and <−1.5: −0.2857 *P − 0.4286<br>≥−1.5 and ≤4.5: 0<br>>4.5 and <7.5: 0.3333 *P − 1.5<br>≥7.5: 1 | ≤−5: 1<br>>−5 and <−1.5: −0.2857 *P − 0.4286<br>≥−1.5 and ≤2.94: 0<br>>2.94 and <5.46: 0.3968 *P − 1.667<br>≥5.46: 1 |

P is the considered property; — means that the 'lead-like' penalty is equal to the 'drug-like' penalty.

The penalty varies from 0 to 1. Only compounds with a sum of the penalty between 0 and 1 have been selected.

By means of this protocol, 507718 compounds have been retrieved and then used in the virtual screening approach.

Virtual Screening

The virtual screening approach used in this study can be described as a virtual docking approach. In fact, compounds derived from the previously described filters were directly used in docking calculations, performed with the software GOLD (Cambridge Crystallographic Data Centre, Cambridge, UK, http://www.ccdc.cam.ac.uk) and the following parameters:

Protein: protein data bank code 1YWT;
Cavity_file: from ligand (BV-01 binding mode, radius 10 Å);
Scoring function: ChemScore (J. Mol. Biol. 1995, 245, 43-53; J. Mol. Biol. 1997, 267, 727-748; Proteins 2003, 52, 609-623);
Search efficiency: 50%;
Num. Runs: 20.

This docking protocol was optimized for maximum speed of calculation according to satisfactory efficiency and it allowed identifying the previously described BV-01 and BV-02 compounds, with a score of at least 35. For this reason, to select compounds after docking calculations, a score value of 35 was applied as a first filter. As a consequence, 1150 compounds have been selected, including BV-01, BV-02 and some of their analogues.

These compounds have been then rescored using three scoring functions, following a protocol optimized for the maximum efficiency:

Scoring function: ChemScore, GoldScore and ASP (Proteins: Struct. Func. And Bioinf., 2005, 61, 272-287);
Search efficiency: 100%;
Num. Runs: 50.

In particular, the compounds have been ranked on the basis of ChemScore, GoldScore and ASP scoring functions, and then reordered applying the rank-by-rank approach, so that only compounds with the best three scores have been selected.

Moreover, with regard to the binding of phosphopeptides the residue R129 of 14-3-3σ plays a pivotal role for the coordination of the phosphate group. Considering the importance of this interaction, compounds not interacting with this residue were discarded. For this purpose, due to the inability to visually inspect a large number of compounds, the average and the minimum distance of each compound from this residue have been calculated and then used as a criteria to filter the selected compounds. Compounds with distance minimum ≥4 Å and average distance ≥10 Å are discarded. After the application of a such filter, the Root Mean Square Deviation (RMSD) values have been computed for each compound between the docking poses derived from ChemScore and GoldScore scoring functions, between the docking poses obtained with ChemScore and ASP scoring functions, and finally between the docking poses from GoldScore and ASP scoring functions. Only compounds with the same binding mode (RMSD <1.5 Å) and the best score value have been selected.

The virtual docking approach provided the general formulas I, II, III, IV and V, as reported above.

Biological Results

Methods:

Cell Lines and Treatments

Parental pro-B murine cell line Ba/F3 and clones expressing the wt and T315I and E255K-mutated Bcr-Abl constructs were kindly donated by Michael W Deininger (Department of Hematology and Clinical Oncology, Health and Science University, Cancer Institute, Portland, Oreg., USA). They were maintained in RPMI medium (Gibco, Paisley, 9 JPET#172536 UK) supplemented with 10% FCS (Gibco), 1% I-glutamine (Sigma, St. Louis, Miss., USA) and 10% WEHI 3 conditioned medium as source of IL-3 when required. Indirect immuno-magnetic labeling (mini-MACS from Milteny Biotech, Bergish Gladback, Germany) was used to isolate CD34+ hematopoietic progenitors from bone marrow samples of 3 CML patients in blast crisis who developed IM resistance. Patient informed consent to use bone marrow samples for our experimental studies was approved by the Ethical Committee of S. Orsola-Malpighi Hospital (Bologna, Italy). The content of CD34+ cells in each sample was measured by cytofluorimetric analysis of CD34 expression with a FacScan (Becton Dickinson, Franklin Land, PI, USA). It was >95% in all cases. D-HPLC and sequencing were used to identify Bcr-Abl point mutations (Soverini, 2005). BV02 cytotoxicy was assayed in clonogenic assays, the best in vitro technique to quantify drug impact on cell reproductive integrity.

Briefly, the authors assessed the reduction of colony (aggregates containing >50 cells generated in 0.9% methylcellulose supplemented with 30% FCS) number in Bcr-Abl-expressing Ba/F3 cell lines and CD34+ in presence of BV02 increasing doses after 7 or 14 day incubation, respectively, at 37° C. in fully humidified atmosphere and 5% CO2. Linear and non linear regression analyses were used to calculate BV02 LD50 in Bcr-Ablexpressing Ba/F3 cell lines and CD34+ progenitors from CML patients, respectively. Apoptosis induction and involved signals were assayed in Bcr-Abl-expressing Ba/F3 cell lines after 24 h exposure to 1 µM IM and 5 µM BV02 by means of cytofluorimetric analysis of Annexin V (Hoffmann-La Roche, Basel, SW) and PI (Sigma) uptake, Western blot and IP/immunoblotting analyses, according to published methods (Mancini, 2009).

Protein Analysis

Western blot and IP/immunoblotting analyses were performed on proteins obtained from whole cells, nuclear fractions and mitochondrial membranes according to published methods (Mancini, 2005; Mancini, 2007). Briefly, whole cell lysates were obtained from 2×107 cells in Buffer A (10 mM Tris pH 8.0, 150 mM NaCl, 10 mM Iodacetamide, 1% Chaps, 0.02% Sodium 10 JPET#172536 Azide supplemented with protease inhibitors: Trypsin and pepsin inhibitors, leupeptin, anti-pain, $Na_3VO_4$ and PMSF [all from Sigma]). Nuclear lysates were obtained from naked nuclei recovered from 2×107 cells kept in buffer B (10 mM NaCl, 5 mM $MgCl_2$, 10 mM phosphate buffer and 0.1% Tergitol-type detergent NP40 [all from Sigma] supplemente with protease inhibitors) by means of 3 sonication rounds (10' pulses using a Hight Intensity Ultrasonic Processor/Sonicator from Cole Parmer [Vernon Hills, Ill., USA] equipped with 2 mm tips). Mitochondrial membranes were separated from whole cell lysates by 30' centrifugation at 14,000 g in 2 mL buffer C (20 mM Hepes pH 7.5, 1.5 mM $MgCl_2$, 10 mM KCl, 1 mM EDTA, 1 mM EGTA, 1 mM dithiothreitol, 0.1% PMS and protease inhibitors in 250 mM sucrose) at 4° C.

Proteins or IP products obtained through overnight incubation with primary antibodies in Buffer D (250 mM NaCl, 15 mM $MgCl_2$ 40 mM Hepes, 60 mM glycerophosphate supplemented with protease inhibitors) were resolved in SDSPAGE. Gels were then transferred onto nitrocellulose membranes (Schleicher & Schuel, Dassel, Germany), labelled with primary and secondary antibodies in TBS with 5% BSA (Sigma) and 0.1% Tween20 (Sigma). The antibodies were purchased from Upstate Biotechnology (Lake Placid, N.Y., USA), Cell Signalling (Danvers, Mass., USA) and Santa Cruz Biotechnology (Santa Cruz, Calif., USA). Signals were visualized by the enhanced chemo-luminescence detection system ECL from Pierce (Rockford, Ill., USA). Signal intensities in single blots obtained from three individual experiments were quantified by mean of a dedicated software (Launch VisionWorks LS, Upland, Calif., USA). Such a sofware attributes a numerical value to signals of chemo-luminescent substrates transferred on highly sensitive radiographic films (Pierce, Rockford, Ill., USA) hence allowing a comparative analysis of protein levels in untreated and drug-exposed samples.

The statistical significance of differences in signal intensities relative to cell treatments was assessed by mean of paired Student's t-test; $p<0.05$ was kept as limit for statistical significance.

Cytofluorimetric Analysis of Cell Cycle Distribution and Caspase 8 Activation

Cell cycle distribution was performed on 1×106 cells fixed overnight in 70% ethanol and treated with 1 µg/µL 11 JPET#172536 PI and RNAse (Sigma) at 37° C. for 30'. PI uptake was measured by mean of a FACScan flow cytometer set at >580 nm and a dedicated software (both from Beckton Dickinson, San Jose, Calif., USA). Caspase-8 activity was detected with a commercial kit (Carboxyfluorescein FLICA Apoptosis Detection kits from Immunochemistry Technologies LLC, Bloomington, Minn., USA) according to manufacturer instructions. Briefly, cells labelled with fluorochrome-bound inhibitor of caspase (FLICA: 300 µL/well at 37° C. for 1 hour in 5% CO2, fully humidified atmosphere) were quantified by means of cytofluorimetric analysis at an excitation range from 488 to 492 nm and an emission range from 515 to 535 nm. Apoptosis was quantified as the level of fluorescence emitted from FLICA probes bound to caspases. Non-apoptotic cells appeared unstained, whereas cells undergoing apoptosis were brightly fluorescent. Caspase-8 activity was quantified by mean of a dedicated software (DIVA from Becton Dickinson). Cell response to BV-01 and BV-02 was evaluated in clonogenic assays (0.9% methylcellulose additioned with drug scalar doses) (see Methods above for methodological details).

Figure 4:
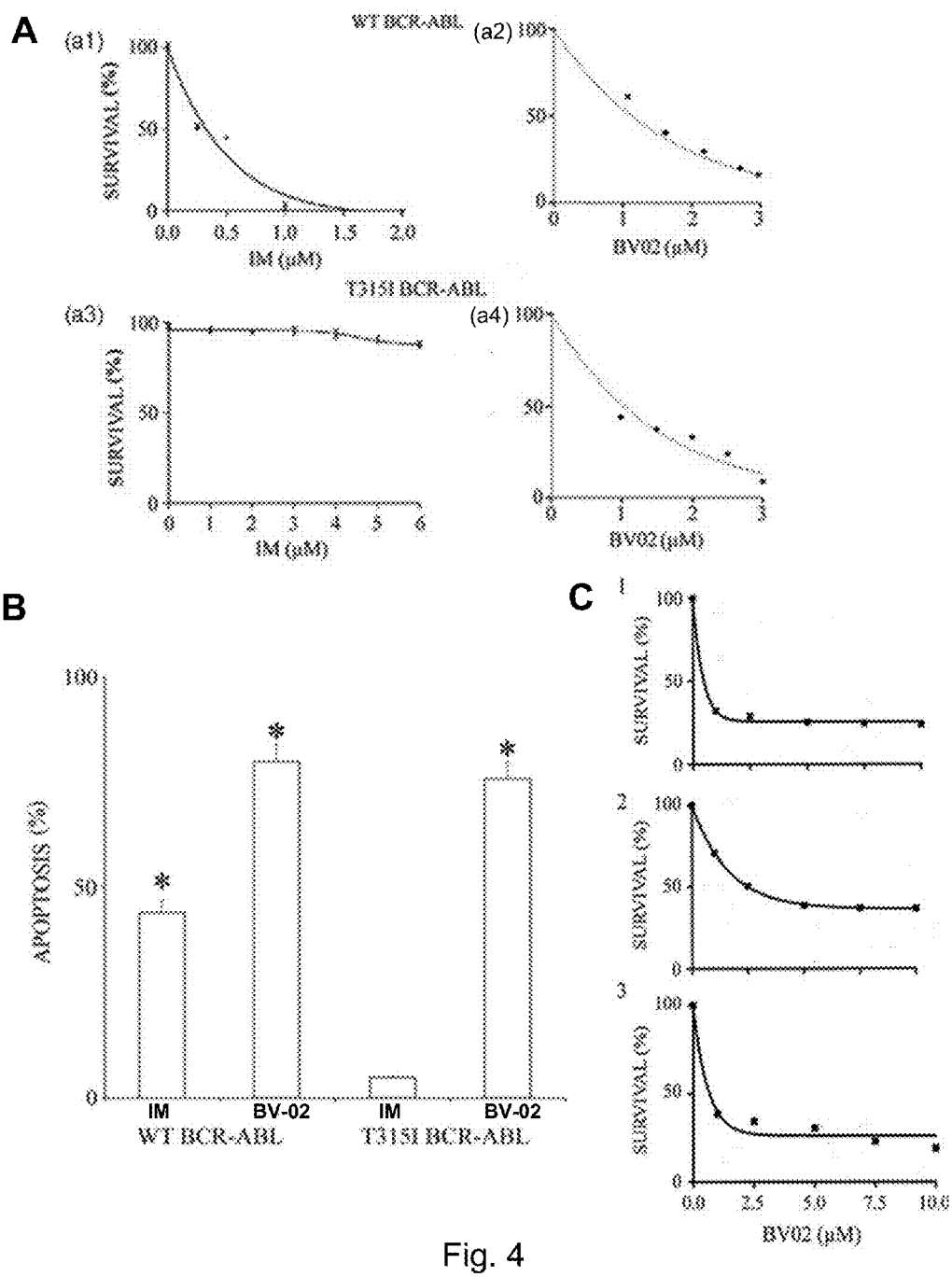
FIG. 4. BV02 effects on Bcr-Abl-expressing cells. A: BV02 impact on reproductive integrity of Ba/F3 cells expressing the wild type Bcr-Abl sensitive to IM (a2) or the T315I mutation resistant to IM (a4). IM response of both cell types was also evaluated (a1 and a3, respectively). Dose-response curves were analyzed by means of linear regression analyses to calculate $LD_{50}$, i.e. the compound dose required to reduce to 50% the cell plating efficiency (aggregates containing >50 cells: % values of vs. untreated controls) in 0.9% methylcellulose. Results shown here represent the mean values of three individual experiments. SD did not exceed 10% (data not shown); B: Cytofluorimetric analysis of Annexin V and PI uptake was used to measure apoptosis induction in response to IM (1 µM for 24 h) and BV02 (5 µM for 24 h) in Ba/F3 cells expressing the wild type Bcr-Abl protein (first and second bar) or the T315 mutation (third and fourth bar). Results shown here represent the mean values±SD of three individual experiments. Apoptotic cell fractions in untreated controls was <5% (data not shown). IM has a statistically significant impact (*) on survival of Ba/F3 cells expressing wt Bcr-Abl construct (p<0.001), but not on survival of Ba/F3 cells expressing T315I mutation (p<0.5). BV02 has a statistically significant impact (*) on survival of both cell types (p<0.0001); C: BV02 survival curves of CD34$^+$ cells isolated from bone marrow samples of 3 CML patients (panel 1, 2 and 3) in blast crisis who developed in vivo IM resistance associated with the outcome of T315I mutation. Non linear regression analysis was used to calculate BV02 $LD_{50}$.

Here, the authors report the effects of BV02 as exemplificative of other tested compounds. BV02 exhibited cytotoxic effects against Ba/F3 Imatinib-sensitive cells expressing the wt Bcr-Abl chimeric protein and also against Ba/F3 cells expressing the Bcr-Abl mutation coding for T315I, which is highly resistant to Imatinib (FIG. 4A).

BV02 lethal doses 50 (LD50, corresponding to the drug dose capable of reducing to 50% cell clonogenic potential) were 1.04±0.09 and 1.47±0.12 µM, respectively on Ba/F3 Imatinib-sensitive cells expressing the wt Bcr-Abl chimeric protein and Ba/F3 cells expressing the Bcr-Abl mutation coding for T315I. By comparison, $LD_{50}$ of Imatinib in Ba/F3 cells expressing the wild type Bcr-Abl construct was 0.4 µM, while >10 µM in Ba/F3 cells expressing the T315I mutation.

As shown in Table 4, BV-01 and BV-02 exhibited about the same cytotoxic effects on parental cell lines (lacking Bcr-Abl) and in Ba/F3 cells expressing the Bcr-Abl mutation coding for E255K.

TABLE 4

| Ba/F3 cytotoxic effects of BV-01 and BV-02. | | | |
|---|---|---|---|
| | LD50 (µM) | | |
| | Ba/F3 Parental | p210Bcr-Abl | |
| | | WT | E255K | T315I |
| BV-01 | 1.89 | 1.41 | 1.28 | 1.70 |
| BV-02 | 1.08 | 1.04 | 1.21 | 1.47 |

BV02 cytotoxicity on IM-sensitive and -resistant Ba/F3 cells was contingent upon the induction of apoptotic cell death (FIG. 4B, where the fort bars of each panel refers to IM-induced apoptotic fraction). BV02 cytotoxicity in an IM-resistant cell context was further confirmed in putative hematopoietic stem cell identified by the $CD34^+$ phenotype isolated from three CML patients in blast crisis who developed resistance to IM in consequence of the outcome of T315I mutation (FIG. 4C).

Figure 5:
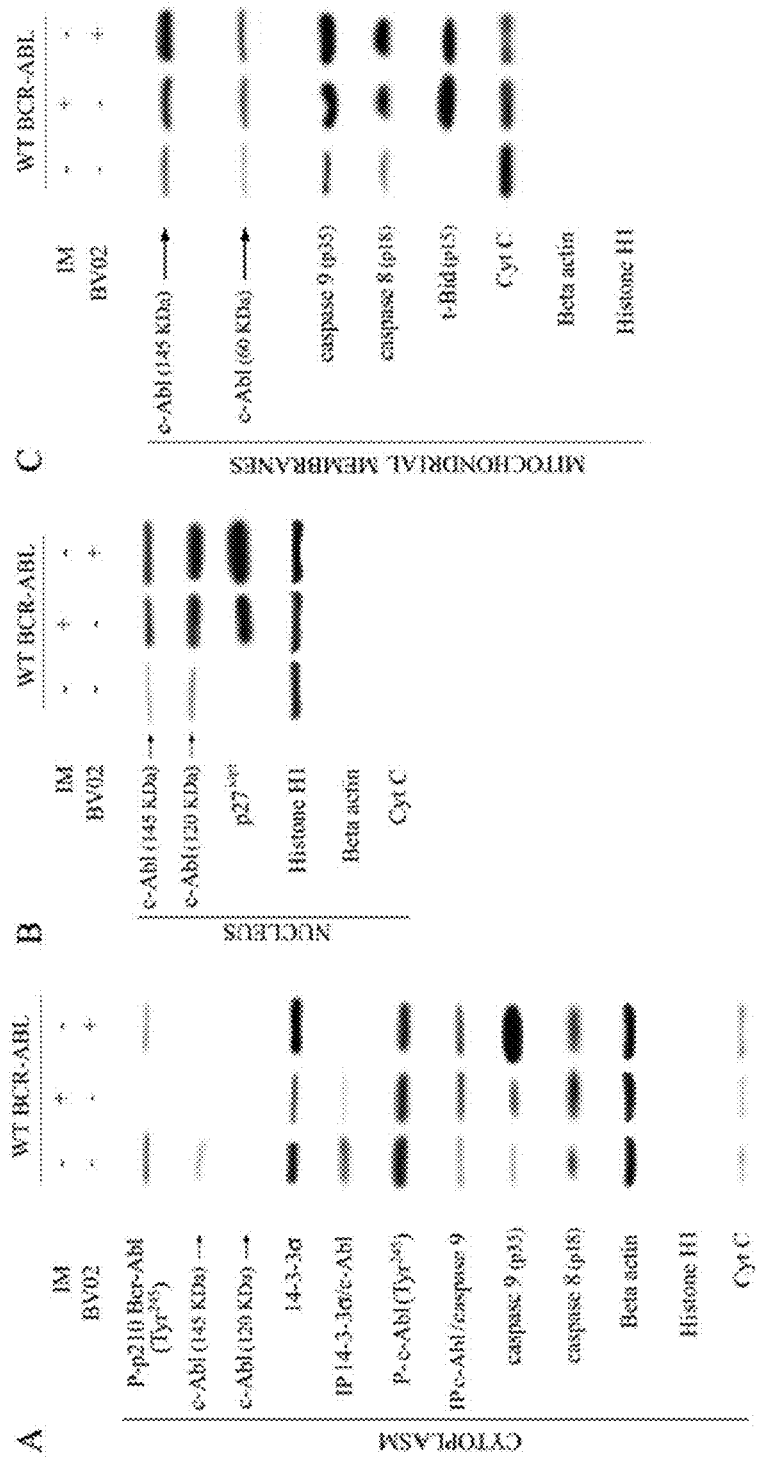
FIG. 5. BV02 effects on c-Abl sub-cellular relocation in wt Bcr-Abl-expressing Ba/F3 cells. Protein expression and interactions in (A) cytoplasmatic compartment, (B) nuclear compartment and (C) at mitochondrial membranes of wild type Bcr-Abl-expressing Ba/F3 cells either untreated or after 24 h exposure to 1 µM IM or 5 µM BV02 were analyzed by mean of Western blot or IP/immunoblotting. Beta actin, histone H1 and Cyt c levels served as controls for protein loading and to exclude cross contamination among the three subcellular compartments. Results identical to those shown here were obtained in two additional experiments. Signal intensities in single blots were measured by a chemoluminescence detection system and quantified by mean of a dedicated software (see Methods section for details). In the cytoplasm (A), BV02 did not significantly affect the phosphorylation of p210 Bcr-Abl at Tyr245 (p<0.1) but the phosphorylation of p210 Bcr-Abl at Tyr245 was completely revoked by IM. c-Abl phosphorylation at Tyr245 was not affected by any of BV02 and IM (p<0.1). The levels of 14-3-3σ were left steady by BV02 (p<0.1) and reduced by IM (p<0.005). BV02 (as well as IM) induce a statistically significant (p<0.05 or less) i) reduction of c-Abl (145 kDa) level, ii) reduction in the interaction between c-Abl and 14-3-3σ, iii) increase in c-Abl interaction with caspase 9, iv) increase in caspase 9 (p35) and caspase 8 (p18) activated fragments. In the nuclear compartment (B), c-Abl (145 and 120 kDa) and p27kip1 were significantly increased by BV02 and IM (p<0.01 or less). At mitochondrial membranes (C), c-Abl (145 and 60 kDa), caspase 9 (p35), caspase 8 (p18) and t-Bid (p15) were significantly raised by BV02 and IM (p<0.01 or less).

Previous studies showed that the nuclear import of c-Abl protein in response to stress is conditional upon its release from 14-3-3 scaffolding proteins as a consequence of their post-translational driven by c-Jun N-terminal kinase (JNK) (Nat Cell Biol, 2005, 7, 278-285). The Bcr-Abl kinase prevents such post-translational modifications hence retaining the protein or residual c-Abl (the one not rearranged with Bcr) in the cytoplasm (Traffic, 2009, 10, 637-647). Accordingly, targeting of 14-4-4 docking site may promote c-Abl release and relocation in sub-cellular compartments where it triggers apoptotic signals, even in cells driven towards IM resistance by Bcr-Abl point mutations. Indeed, BV02 induced c-Abl release from 14-3-3σ and its relocation in the nuclear compartment and at mitochondrial membranes, followed by the chain of events that elicit apoptotic cell death (including the transcriptional activation of c-Abl downstream genes and the dissipation of mitochondrial membranes leading to cytochrome c release and caspase activation). Western blot or immunoprecipitation (IP)/immunoblotting technique (see above Methods for methodological details) let see that BV-02 (5 μM for 24 h) mediates c-Abl release from 14-3-3σ in a way similar to that found in response to treatment with Imatinib (1 μM for 24 h) through events encompassing 14-3-3σ phosphorylation by c-Jun N-terminal kinase (FIG. 5A). Once released, c-Abl is imported into the nuclear compartment, where it triggers the transcription of pro-apoptotic genes. c-Abl nuclear import concerned the whole length protein (145 kDa) and the p120 kDa fragment generated by interaction with caspase 9 (FIG. 5B). The significant increase of cyclin-dependent kinase inhibitor p27$^{Kip1}$ in response to BV-02 suggests that a common mechanism for the nuclear import of proteins involved in cell proliferation and survival could be based on their release from 14-3-3. Moreover, BV-02-induced c-Abl translocation to mitochondrial membranes in the full-length and caspase-induced cleaved isoforms (mainly the 60 kDa fragment, FIG. 5C). At this level, c-Abl integration was associated with a significant increase of caspase 8 (18 kDa) and caspase 9 (35 kDa) cleaved fragments, a critical event for their dissipation in response to BV-02 (FIG. 5A).

Figure 6:
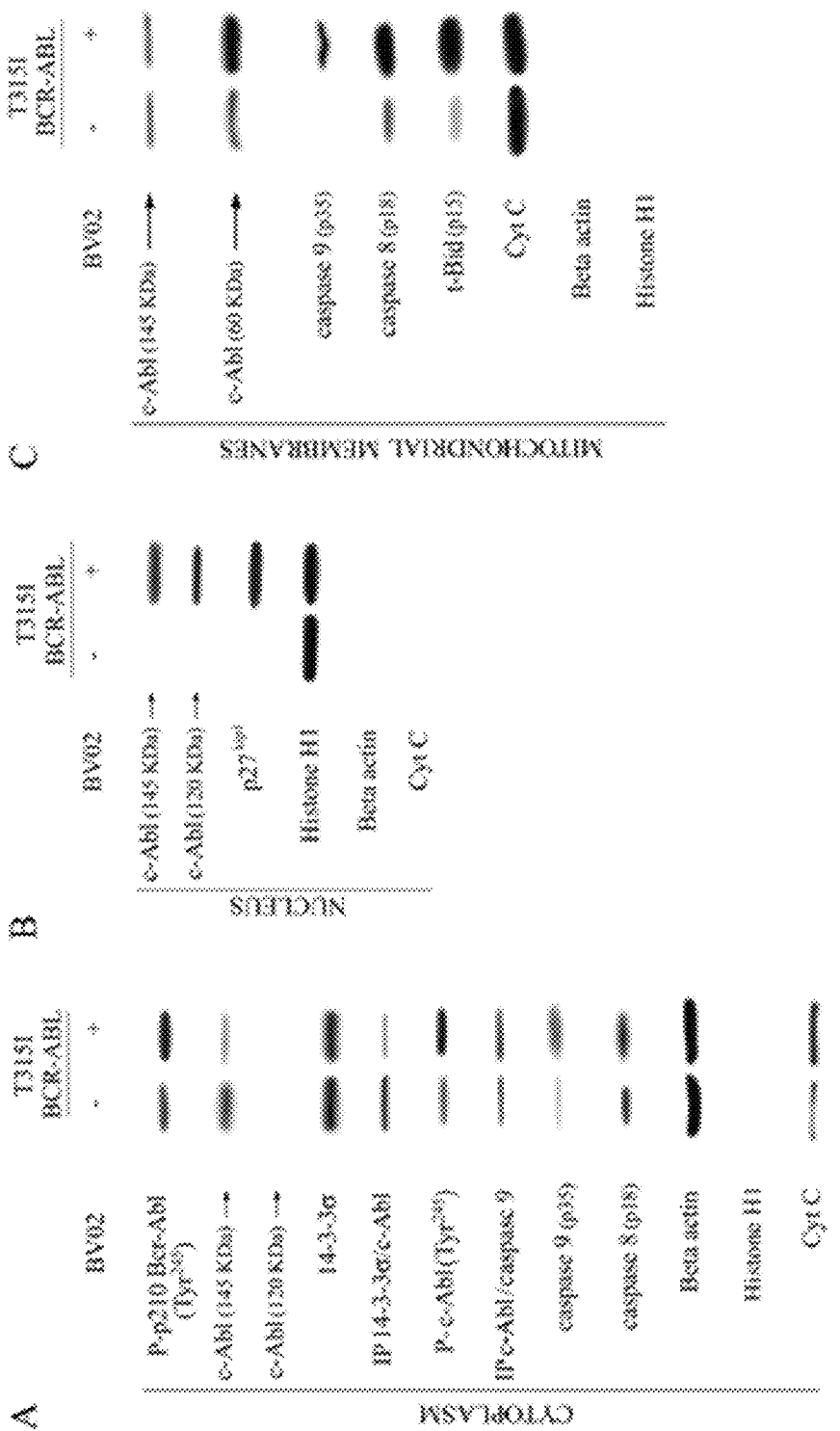
FIG. 6. BV02 effects on c-Abl sub-cellular relocation in Ba/F3 cells expressing T315I Bcr-Abl mutation. See legend to FIG. 5 for details. A slight increase (p<0.05) in Tyr245 phosphorylation of normal and Bcr-rearranged c-Abl was apparent in Ba/F3 cells expressing the T315I mutation after exposure to BV02.

BV02 elecited all above mentioned events also in Ba/F3 cell line expressing the T315I Bcr-Abl mutation (FIG. 6 A-C).

Similar biological results were obtained for the compound BV-101.

NMR Experiments

Figure 7:
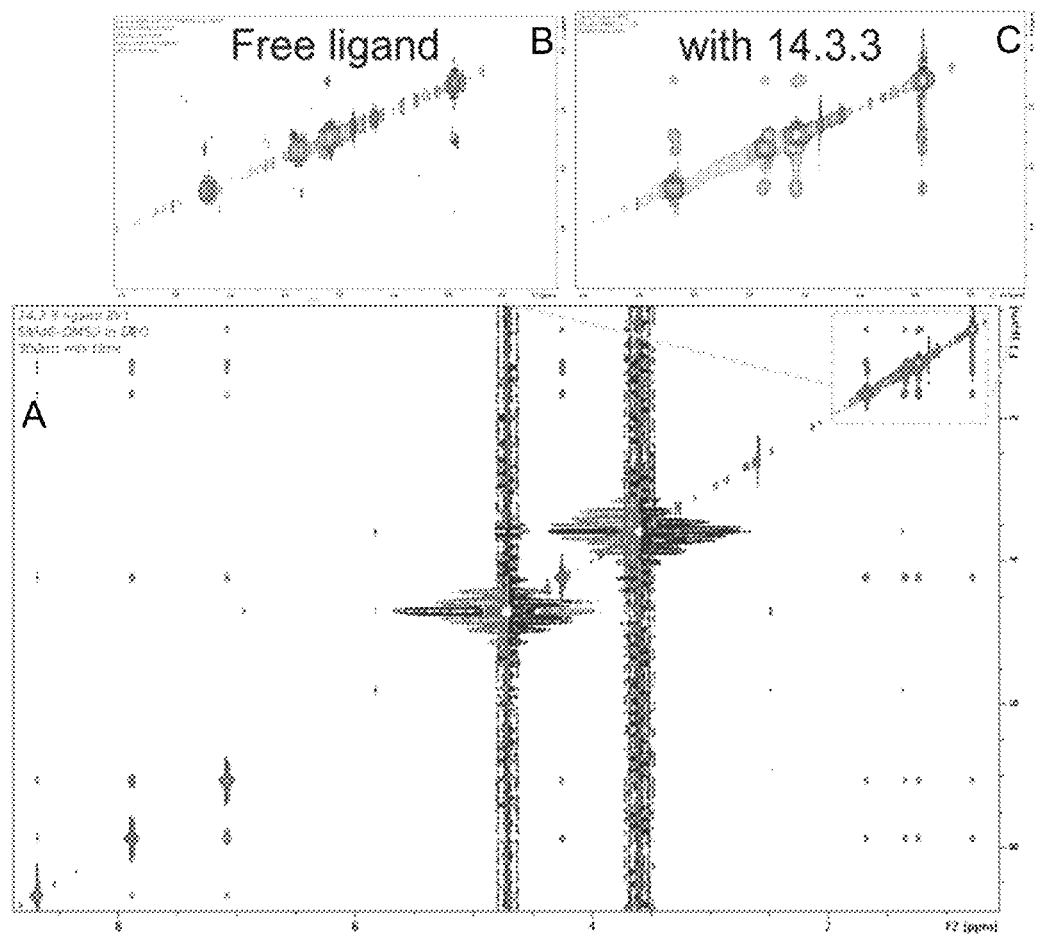
FIG. 7. (A) The 2D homonuclear experiment shows the tr-NOEs between ligand and protein. The highlighted regions show the difference between the spectra recorded on the free ligand (B) and in presence of the protein (C).

The binding ability of BV-01 was analyzed by transferred Nuclear Overhauser Enhancement experiments (tr-NOEs). Experiments were recorded (at 298K on Bruker Avance 600) both on the free ligand and in the presence of protein in concentration 10 fold less than ligand. In the tr-NOEs experiments, only ligands in fast exchange between the bound and the free form are observed. Since the NOE effects are directly related to the size of the molecule in solution, by binding to the protein, the ligands NOE change in intensity and appearance allowing an easy detection of the binding. The 2D homonuclear experiment shows the tr-NOEs between BV-01 and the protein 14-3-3σ (FIG. 7A). The highlighted region shows the difference between the spectra recorded with (FIG. 7C) and without 14-3-3σ (FIG. 7B). The tr-NOEs pattern indicates a weak interaction between ligand and protein.

CONCLUSIONS

This invention describes new 14-3-3 inhibitors having affinity for 14-3-3 active site and preventing the binding with c-Abl. They represent the first non-peptidic inhibitors targeting 14-3-3 proteins, as such they are a helpful strategy to enhance the effects of traditional inhibitors of the oncogenic Bcr-Abl protein.

What is claimed is:

1. A method for treating chronic myeloid leukemia or Imatinib-resistant chronic myeloid leukemia comprising administering to a mammal in need thereof an effective amount of compound BV-02

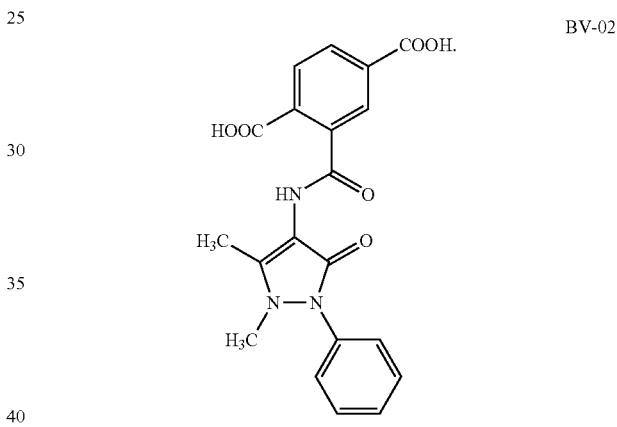

2. The method of claim 1 wherein said compound BV02 is present as a pharmaceutically acceptable salt, solvate, or hydrate.

3. The method of claim 1 wherein said compound BV02 is part of a pharmaceutical composition containing a pharmaceutically acceptable carrier, diluents or excipients.

* * * * *